(12) United States Patent
McKay et al.

(10) Patent No.: US 7,550,011 B2
(45) Date of Patent: Jun. 23, 2009

(54) OSTEOGENIC PACKING DEVICE AND METHOD

(75) Inventors: William F. McKay, Memphis, TN (US); Bradley T. Estes, Durham, NC (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 712 days.

(21) Appl. No.: 10/889,655

(22) Filed: Jul. 12, 2004

(65) Prior Publication Data

US 2004/0254583 A1  Dec. 16, 2004

Related U.S. Application Data

(62) Division of application No. 10/040,154, filed on Oct. 22, 2001, now Pat. No. 6,780,192.

(60) Provisional application No. 60/242,934, filed on Oct. 24, 2000.

(51) Int. Cl.
    *A61F 2/44* (2006.01)
(52) U.S. Cl. .................................. 623/17.16
(58) Field of Classification Search ............... 606/76, 606/77; 433/172–176, 201.1; 604/64, 502, 604/518–519
    See application file for complete search history.

(56) References Cited

U.S. PATENT DOCUMENTS

| | | | |
|---|---|---|---|
| 3,867,728 A | | 2/1975 | Stubstad |
| 4,004,565 A | * | 1/1977 | Fischer et al. .................. 124/45 |
| 4,277,184 A | * | 7/1981 | Solomon ..................... 366/139 |
| 4,375,810 A | | 3/1983 | Belykh |
| 4,501,269 A | | 2/1985 | Bagby |
| 4,518,384 A | * | 5/1985 | Tarello et al. ................. 604/61 |
| 4,532,661 A | * | 8/1985 | Halpern .................... 623/23.14 |
| 4,668,295 A | * | 5/1987 | Bajpai ......................... 106/690 |
| 4,736,738 A | | 4/1988 | Lipovsek et al. |
| 4,863,476 A | | 9/1989 | Shepperd |
| 4,878,915 A | | 11/1989 | Brantigan |
| 4,919,666 A | | 4/1990 | Buchhorn |
| 4,961,740 A | | 10/1990 | Ray et al. |
| 4,992,226 A | * | 2/1991 | Piez et al. .................... 264/109 |

(Continued)

FOREIGN PATENT DOCUMENTS

DE       4409836 A       9/1995

(Continued)

OTHER PUBLICATIONS

Minns, R.J. "Preliminary Design and Experimental Studies of a Novel Soft Implant for Correcting Sagittal Plane Instability in the Lumbar Spine" *SPINE* vol. 22, No. 16, pp. 1819-1827 (1997).

*Primary Examiner*—Eduardo C Robert
*Assistant Examiner*—Nicholas Woodall

(57) ABSTRACT

An osteogenic material packing device is used to pack osteogenic material onto a spinal fusion device. The packing device has a cavity defined therein, which is adapted to receive the spinal fusion device. The packing device further includes an access port, which intersects the cavity to receive the osteogenic material. A cannula is coupled to the packing device and an inserter is coupled to the fusion device in order to insert the fusion device into the packing device. Osteogenic material is packed through the access port around the fusion device. The fusion device then is slid through the cannula and inserted in the intervertebral space between adjacent vertebrae.

24 Claims, 16 Drawing Sheets

U.S. PATENT DOCUMENTS

| | | | |
|---|---|---|---|
| 5,015,247 A | 5/1991 | Michelson | |
| 5,141,510 A | 8/1992 | Takagi | |
| 5,207,710 A | 5/1993 | Chu | |
| 5,219,363 A | 6/1993 | Crowninshield | |
| 5,236,456 A | 8/1993 | O'Leary et al. | |
| 5,258,029 A | 11/1993 | Chu | |
| 5,298,254 A | 3/1994 | Prewett | |
| 5,336,223 A | 8/1994 | Rogers | |
| 5,348,026 A | 9/1994 | Davidson | |
| 5,390,683 A | 2/1995 | Pisharodi | |
| 5,397,364 A | 3/1995 | Kozak | |
| 5,423,816 A | 6/1995 | Lin | |
| 5,423,817 A | 6/1995 | Lin | |
| 5,433,718 A | 7/1995 | Brinker | |
| 5,443,515 A | 8/1995 | Cohen | |
| 5,484,410 A * | 1/1996 | Kriesel et al. | 604/89 |
| 5,484,437 A | 1/1996 | Michelson | |
| 5,489,307 A | 2/1996 | Kuslich et al. | |
| 5,505,732 A | 4/1996 | Michelson | |
| 5,507,813 A | 4/1996 | Dowd et al. | |
| 5,520,923 A | 5/1996 | Tjia | |
| 5,562,736 A | 10/1996 | Ray et al. | |
| 5,571,184 A | 11/1996 | DeSatnick | |
| 5,584,877 A | 12/1996 | Miyake | |
| 5,584,880 A | 12/1996 | Martinez | |
| 5,597,897 A * | 1/1997 | Ron et al. | 530/350 |
| 5,618,286 A | 4/1997 | Brinker | |
| 5,645,591 A | 7/1997 | Kuberasampath et al. | |
| 5,645,598 A | 7/1997 | Brosnahan, III | |
| 5,676,699 A | 10/1997 | Gogolewski | |
| 5,693,100 A | 12/1997 | Pisharodi | |
| 5,709,683 A * | 1/1998 | Bagby | 623/16.11 |
| 5,718,707 A | 2/1998 | Mikhail | |
| 5,766,253 A | 6/1998 | Brosnahan | |
| 5,797,909 A | 8/1998 | Michelson | |
| 5,910,315 A | 6/1999 | Stevenson et al. | |
| 6,280,474 B1 * | 8/2001 | Cassidy et al. | 623/16.11 |
| 2005/0171554 A1 * | 8/2005 | Estes et al. | 606/104 |

FOREIGN PATENT DOCUMENTS

| | | |
|---|---|---|
| EP | 0577179 A | 1/1994 |
| EP | 0732093 A | 9/1996 |
| EP | 0796593 A2 | 9/1997 |
| FR | 2712486 A | 5/1995 |
| WO | WO 91/06266 A | 5/1991 |
| WO | WO 91/11148 | 8/1991 |
| WO | WO 94/07441 | 4/1994 |
| WO | WO 95/00082 | 1/1995 |
| WO | WO 95/17861 A | 7/1995 |
| WO | WO 92/14423 | 9/1995 |
| WO | WO 95/25485 A | 9/1995 |
| WO | WO 96/27321 | 9/1996 |
| WO | WO 95/31948 | 11/1996 |
| WO | WO 96/40014 A | 12/1996 |
| WO | WO 97/23174 A | 7/1997 |
| WO | WO 97/30666 | 8/1997 |
| WO | WO 97/37619 | 10/1997 |
| WO | WO 98/04217 A | 2/1998 |
| WO | WO 98/55052 | 12/1998 |
| WO | WO 99/29271 | 6/1999 |
| WO | WO 00/42898 | 7/2000 |
| WO | WO 01/13822 A1 | 3/2001 |

* cited by examiner

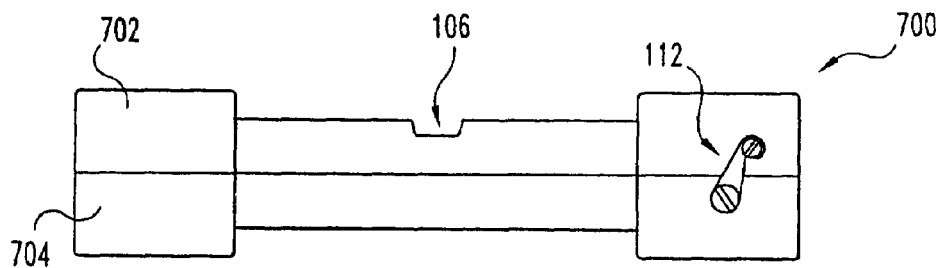
Fig. 7
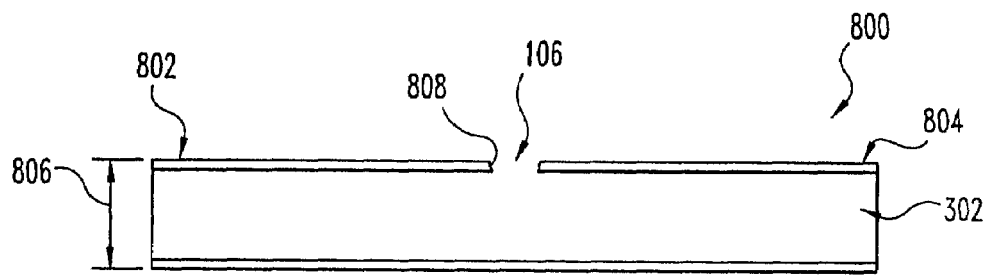
Fig. 8
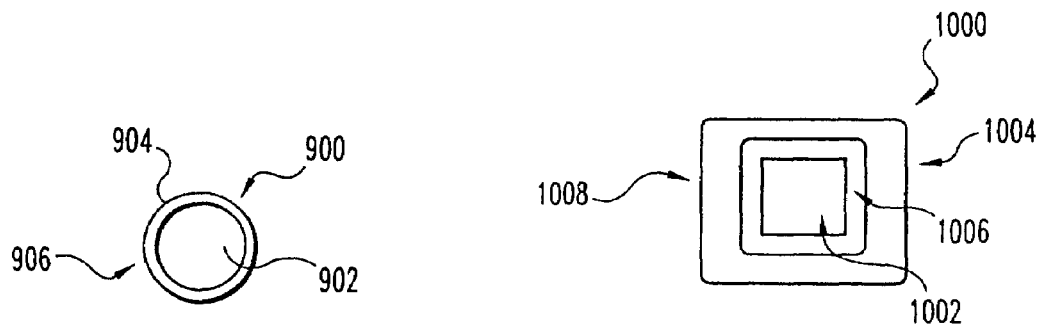
Fig. 9  Fig. 10

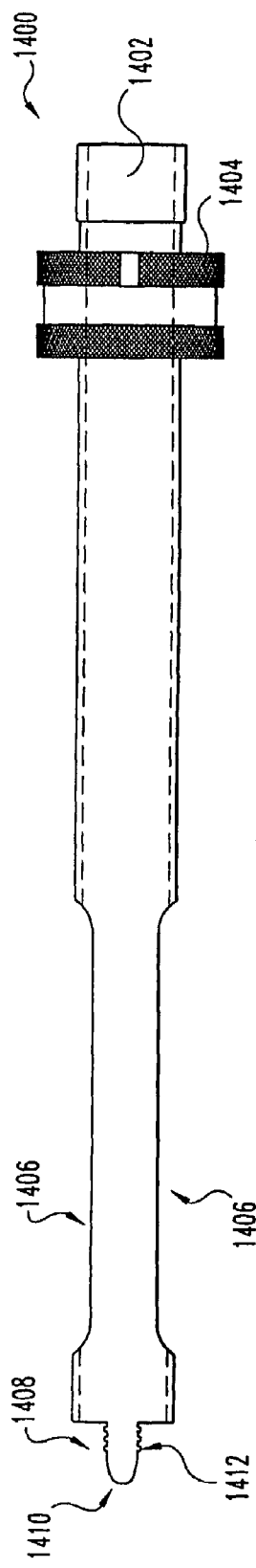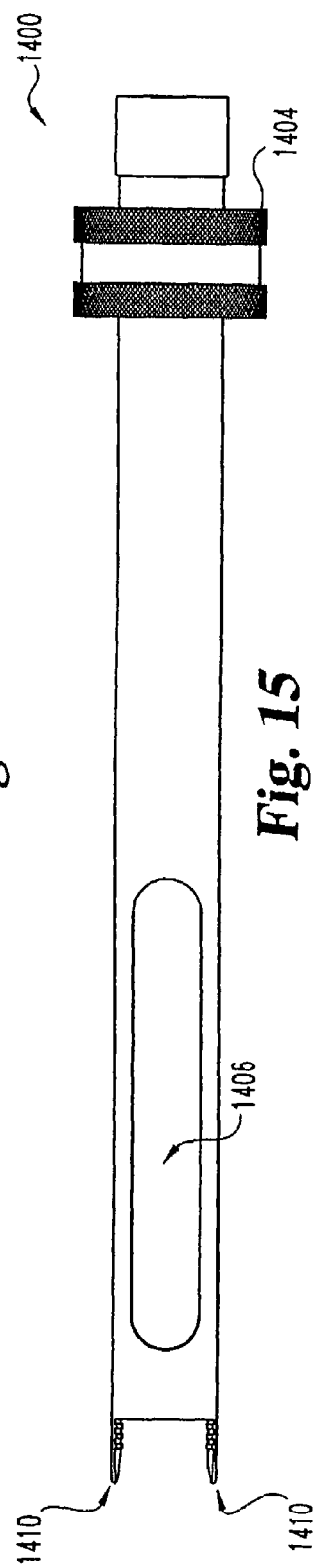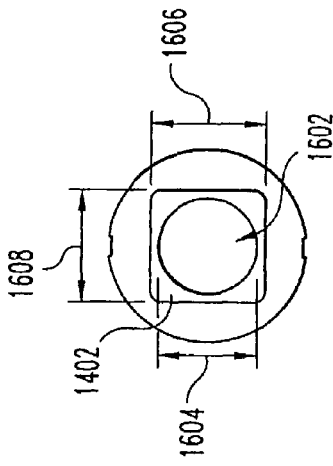
*Fig. 14*   *Fig. 15*   *Fig. 16*

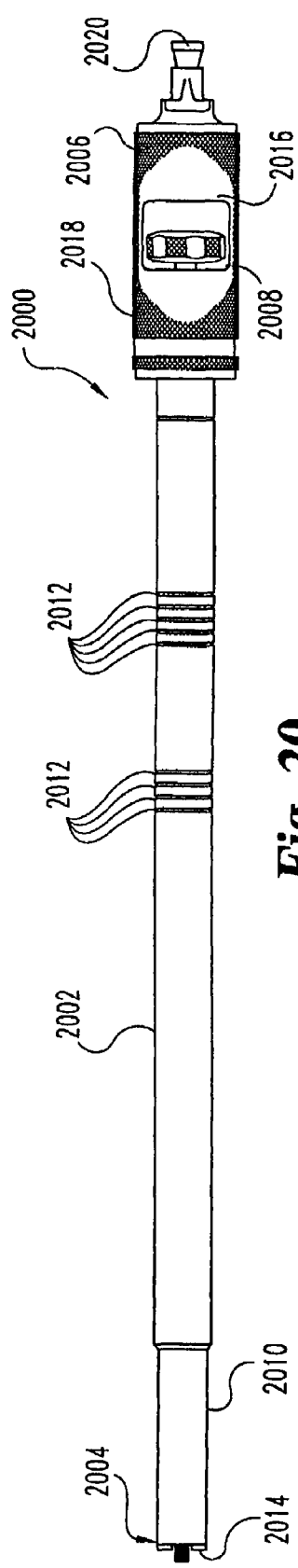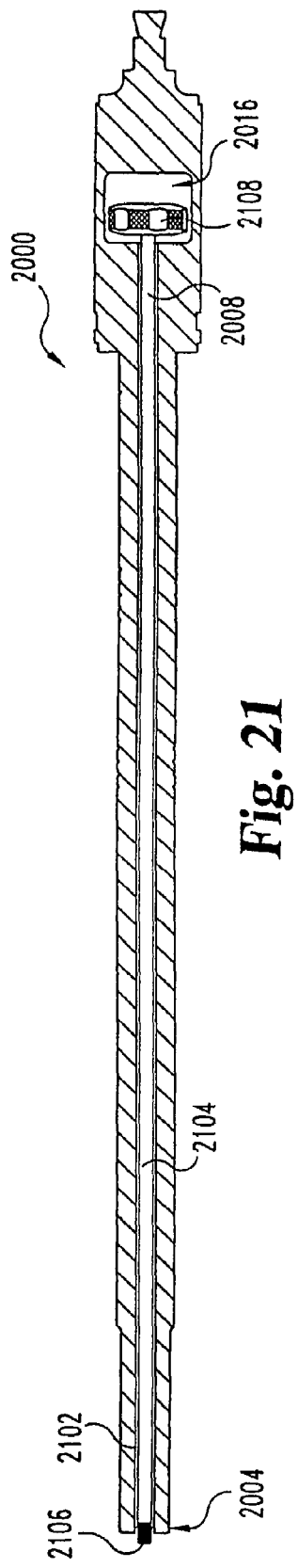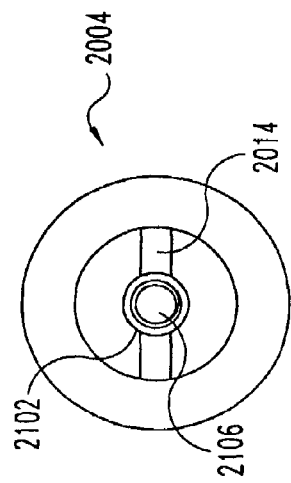
Fig. 20
Fig. 21
Fig. 22

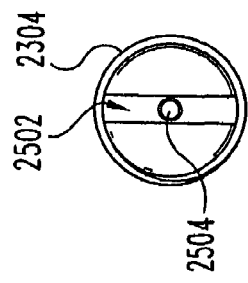
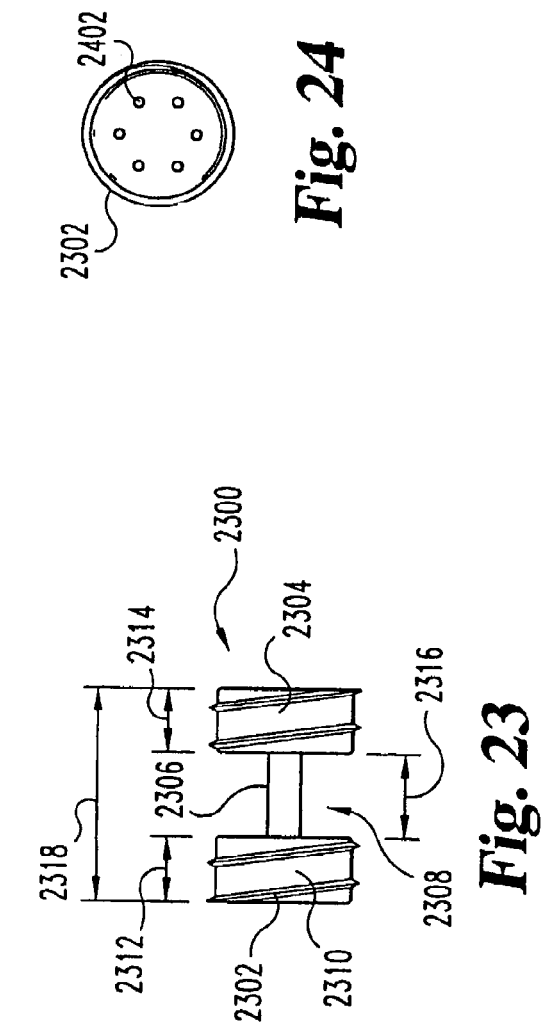
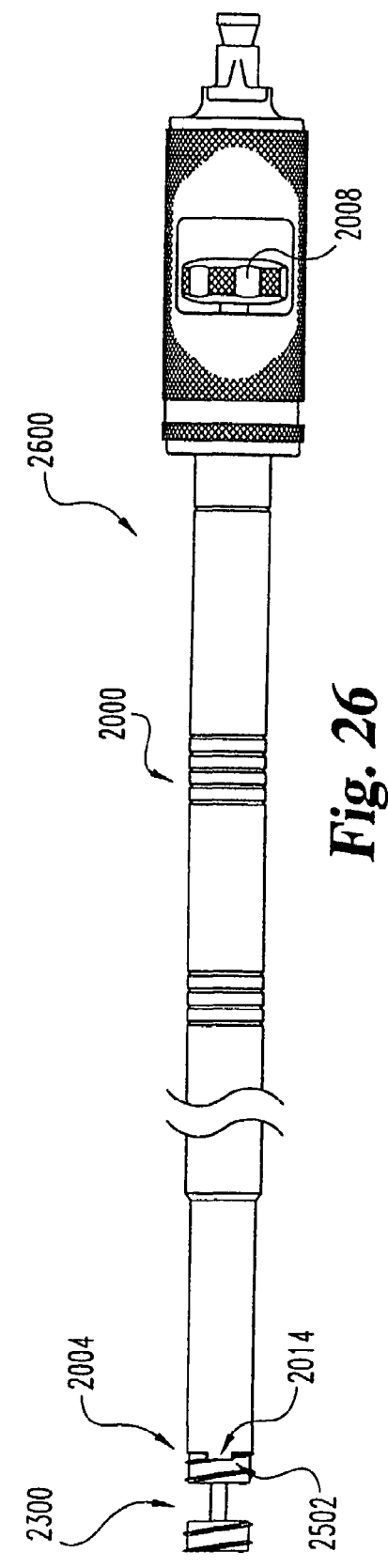

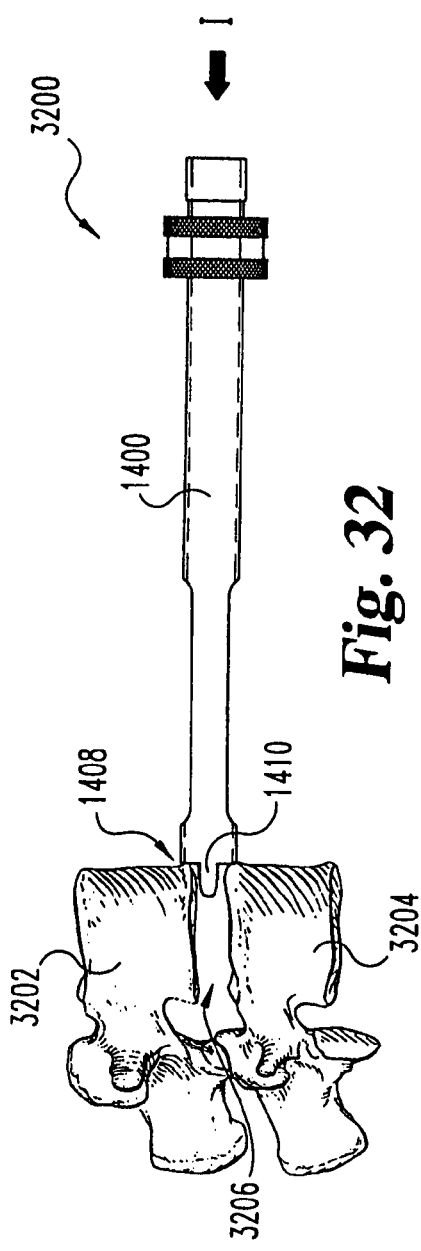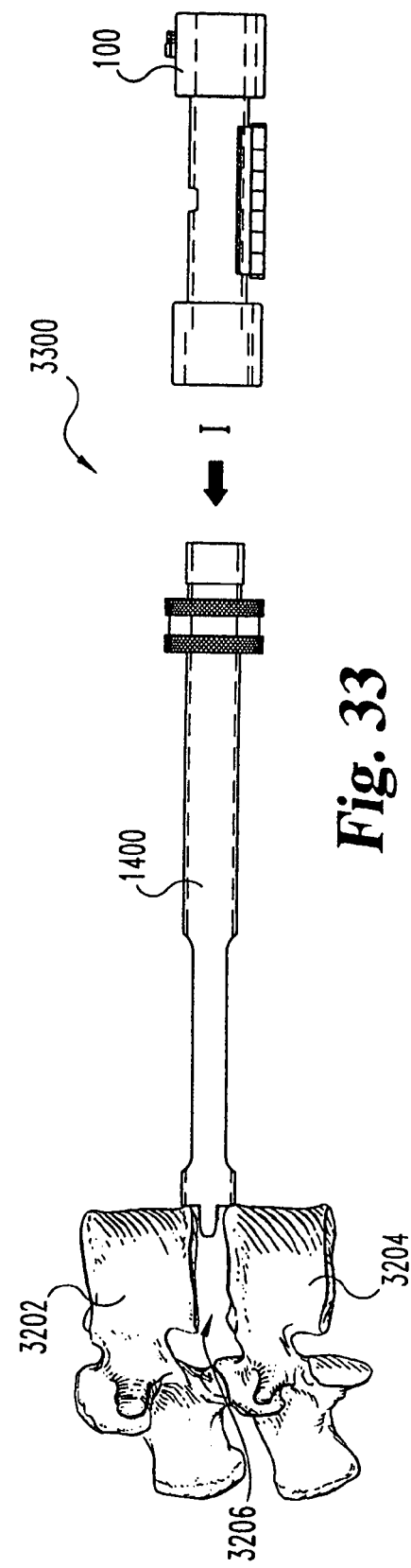
Fig. 32
Fig. 33

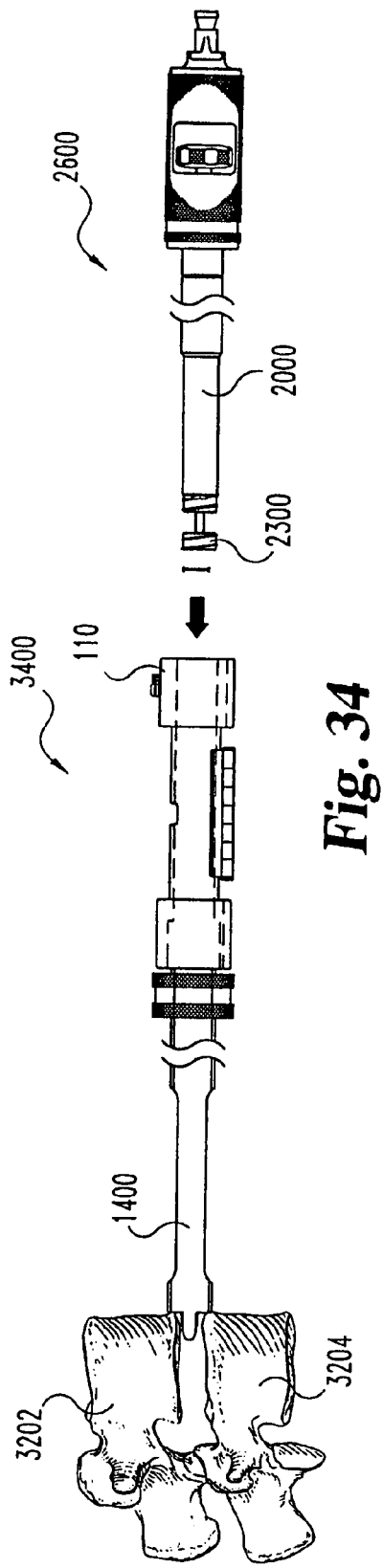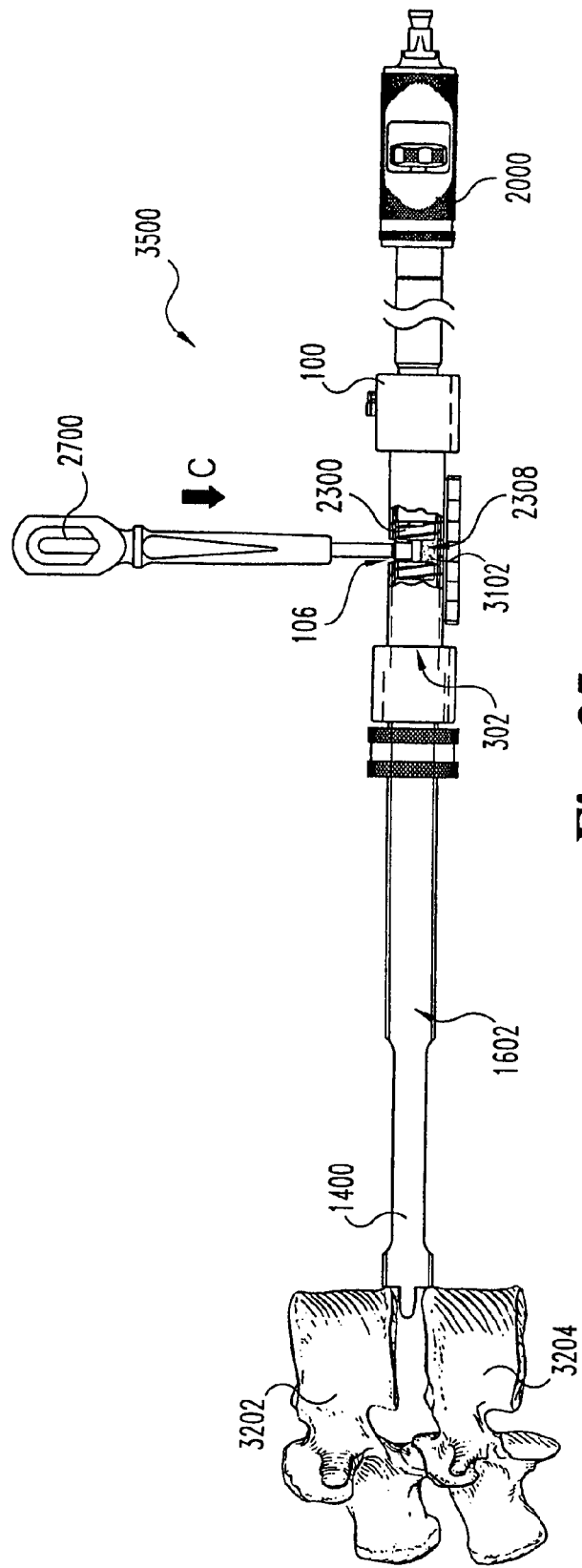

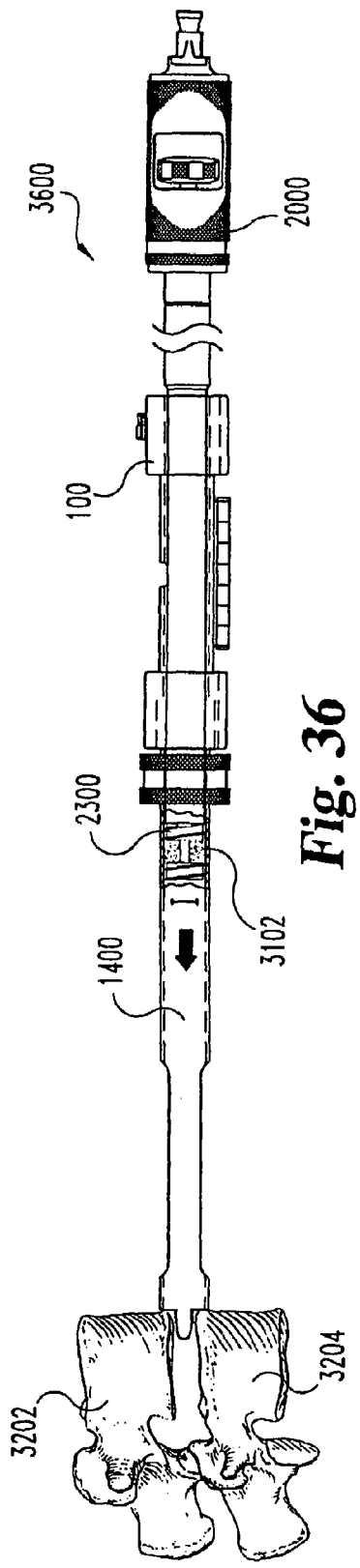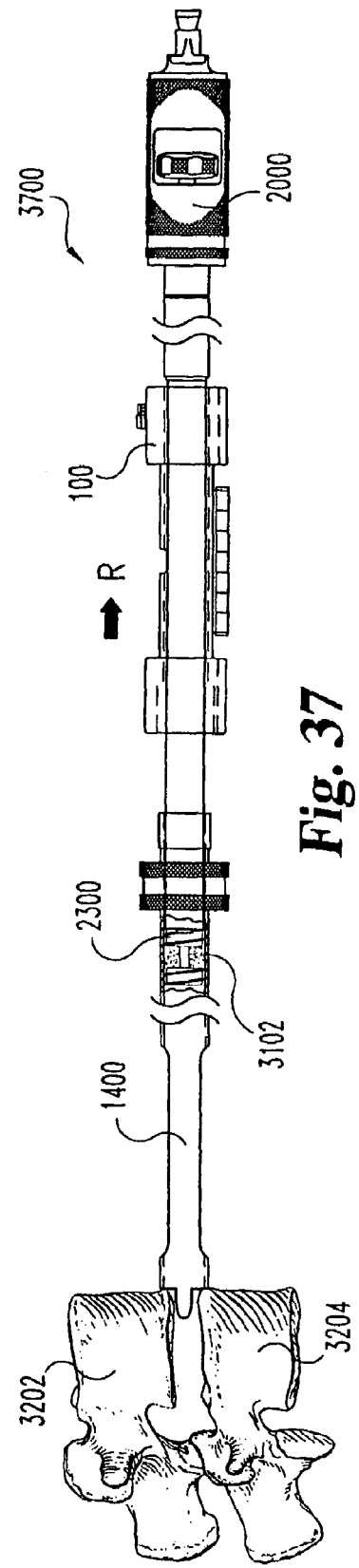

OSTEOGENIC PACKING DEVICE AND METHOD

CROSS-REFERENCE TO RELATED APPLICATIONS

The present application is a divisional of U.S. patent application Ser. No. 10/040,154, filed Oct. 22, 2001 now U.S. Pat. No. 6,780,192, which claims the benefit of U.S. Provisional Patent Application No. 60/242,934, filed Oct. 24, 2000, which are hereby incorporated by reference in their entirety.

BACKGROUND OF THE INVENTION

The present invention generally relates to a device and method for packing material around an object, and more specifically, but not exclusively, relates to a packing device and a method for packing osteogenic material onto a spinal implant.

In many cases, lower back pain originates from damage or defects in the spinal disc between adjacent vertebrae. The disc can be herniated or can be affected by a variety of degenerative conditions. In many cases, these pathologies affecting the spinal disc can disrupt the normal anatomical function of the disc. In some cases, this disruption is significant enough that surgical intervention is indicated.

In one such surgical treatment, the affected disc is essentially removed and the adjacent vertebrae are fused together. In this treatment, a discectomy procedure is conducted to remove the disc nucleus while retaining the annulus. Since the disc material has been removed, a body must be placed within the intervertebral space to prevent the space from collapsing.

In early spinal fusion techniques, bone material, or bone osteogenic fusion devices, were simply disposed between adjacent vertebrae, typically at the posterior aspect of the vertebrae. With such implants, osteogenic material is packed around the implant after the implant is inserted into the intervertebral space. The osteogenic material helps to promote fusion between the adjacent vertebrae. However, packing the osteogenic material around the implant after the implant is inserted can be problematic. For example, a physician may not be able to adequately view whether an adequate amount of osteogenic material is packed around the implant. Further, the osteogenic material may not be tightly bound together. Portions of the osteogenic material may fall out during packing. This can lead to osteogenic debris floating within the patient, which can lead to complications.

In light of this background, there remain needs for improved devices and methods useful in the conduct of spinal fusions and other similar surgeries. The present invention addresses these needs.

SUMMARY OF THE INVENTION

One form of the invention is a unique osteogenic packing device. Another form of the present invention is directed to a unique method for loading osteogenic material.

In another form, the present invention is directed to a unique osteogenic material packing device for packing osteogenic material onto a spinal fusion device. The packing device has a cavity defined therein and is adapted to receive the spinal fusion device. The packing device further has an access port that intersects the cavity for receiving the osteogenic material.

In another form, the present invention is directed to a unique method of loading osteogenic material onto a spinal fusion device. The fusion device is inserted into a cavity of a packing device that includes an access port. The osteogenic material is provided through the access port and onto the fusion device.

In still yet another form, the present invention is directed to unique spinal fusion devices having osteogenic material compacted thereupon, advantageously in a configuration to contact adjacent vertebrae upon implantation of the fusion device.

Further objects, features, benefits, aspects, and advantages of the present invention shall become apparent from the detailed drawings and descriptions provided herein.

BRIEF DESCRIPTION OF THE DRAWINGS

FIG. 7 shows a side view of a packing device with an access port provided in one section.

FIG. 8 shows a cross sectional view of a packing device in accordance with still yet another embodiment of the present invention.

FIG. 9 shows an end view of a packing device with a circular cavity.

FIG. 10 shows an end view of a packing device with a square cavity.

FIG. 14 shows a side view of a cannula.

FIG. 15 shows a top view of the cannula of FIG. 14.

FIG. 16 shows an end view of the cannula of FIG. 14.

FIG. 20 shows a side view of an inserter.

FIG. 21 shows a cross-sectional view of the inserter of FIG. 20.

FIG. 22 shows an end view of one end of the inserter of FIG. 20.

FIG. 23 shows a side view of a fusion device.

FIG. 24 shows an end view of one end of the fusion device of FIG. 23.

FIG. 25 shows an end view of the other end of the fusion device of FIG. 23.

FIG. 26 shows a side view of the fusion device of FIG. 23 coupled to the inserter of FIG. 20.

FIG. 32 shows a side view of a cannula inserted between adjacent vertebrae.

FIG. 33 shows a side view of the assembly of FIG. 32 along with the packing device of FIG. 1.

FIG. 34 shows a side view of an inserter and the assembly shown in FIG. 33.

FIG. 35 shows a partial cross-sectional view of osteogenic material packed around a fusion device.

FIG. 36 shows a partial cross-sectional view of the fusion device in the cannula.

FIG. 37 shows a partial cross-sectional view of the packing device separated from the cannula.

DESCRIPTION OF THE PREFERRED EMBODIMENTS

Figure 1:
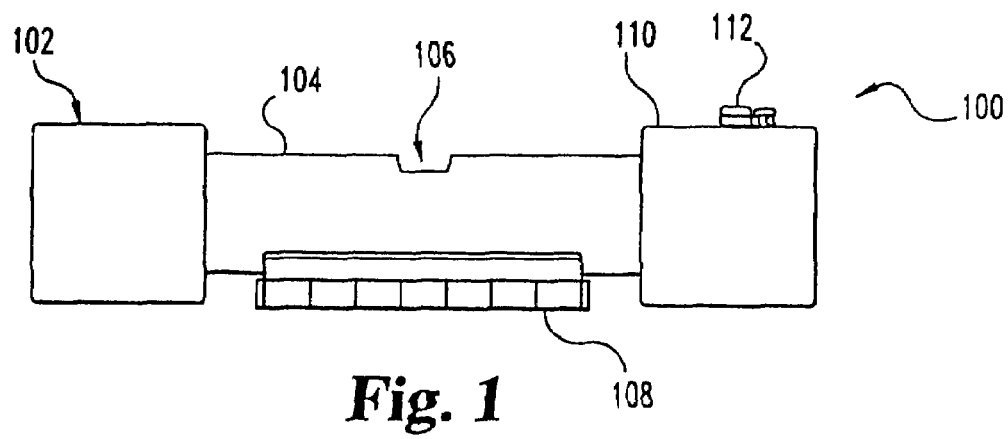
FIG. 1 shows a side view of an osteogenic material packing device in accordance with one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

An osteogenic material packing device 100 in accordance with one embodiment of the invention is depicted in FIGS. 1-6. As shown in FIG. 1, the packing device 100 includes a cannula coupling portion 102, a body portion 104, an access port 106, a connection member 108, an insert receiving portion 110, and a locking mechanism 112. The body portion 104 connects the coupling portion 102 to the insert-receiving portion 110. The port 106 is defined in the body portion 104. It should be understood that the cannula coupling portion 102, the body portion 104, and the insert-receiving portion 110 can have other shapes. In one form, the body portion 104 has a cylindrical shape, and the receiving and coupling portions 102, 112 have a cubic shape. This cubic shape minimizes the risk that the packing device 100 will be damaged by rolling off a surface. It is contemplated that these portions 102, 104, and 110 could be integrated to have a single shape.

Figure 2:
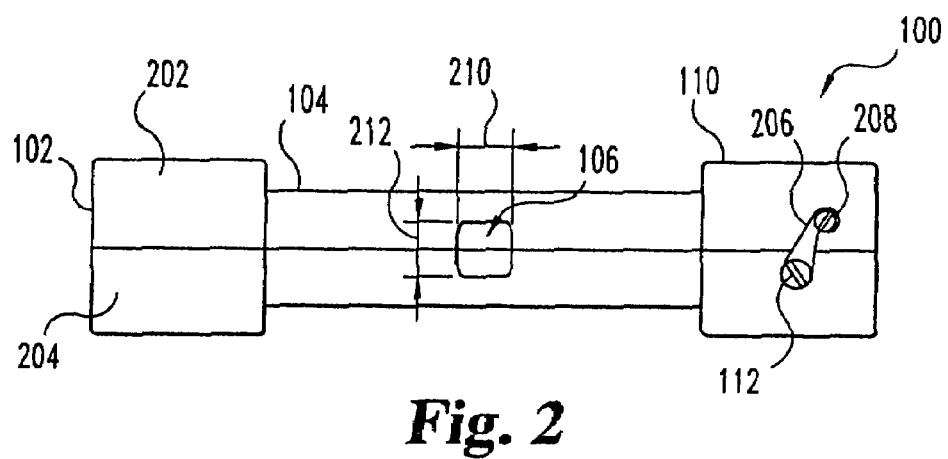
FIG. 2 shows a top view of the packing device of FIG. 1.

As shown in FIG. 2, the packing device 100 has two separate sections 202 and 204. It should be understood that the packing device 100 could be a single piece or can be sectioned in other manners. The two separate sections 202, 204 are coupled together with a connection member 108 and a locking mechanism 112. The connection member 108 in one embodiment is a hinge. The locking mechanism 112 in one form of the invention is a latching mechanism. The locking mechanism 112 includes a hook 206 that engages a pin 208 to lock the two sections 202, 204 together. It should be appreciated that other types of locking mechanisms can also be used. As shown, the port 106 is defined by both sections 202 and 204, and the port 106 has a length 210 and a width 212 large enough to allow osteogenic material to be packed around a fusion device.

Figure 3:
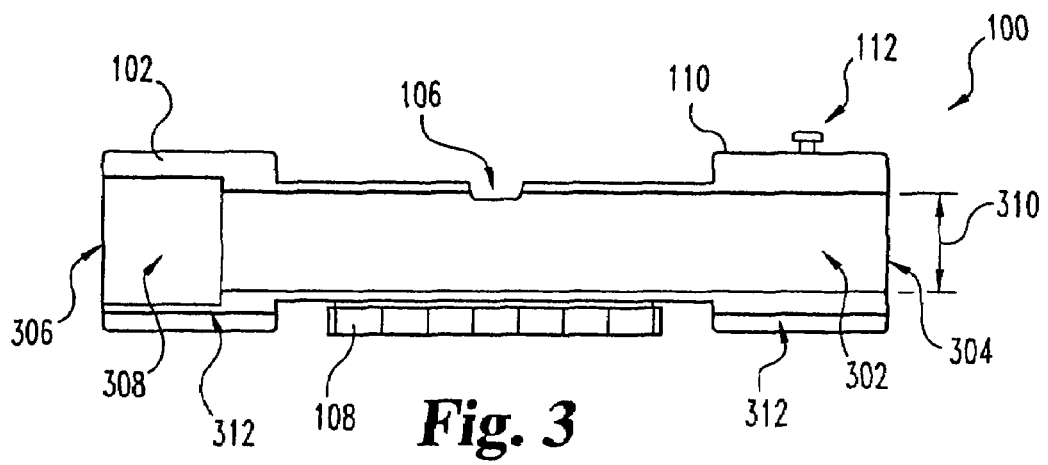
FIG. 3 shows cross sectional view of the packing device of FIG. 1.

A cross-sectional view of the packing device 100 is shown in FIG. 3. A cavity 302 is defined in the packing device 100. The access port 106 opens into the cavity 302. It should be appreciated that the cavity 302 can have a single opening, multiple openings, or no openings. The cavity 302 in one embodiment has openings 304, 306 at opposite ends of the device 100. In addition, the cavity 302 has a cylindrical shape to accommodate a fusion device with a cylindrical shape. The cavity 302 has a diameter 310 such that the fusion device can fit inside and slide along the cavity 302. It should be appreciated that the cavity 302 can have other shapes in order to accommodate differently shaped fusion devices.

Figure 4:
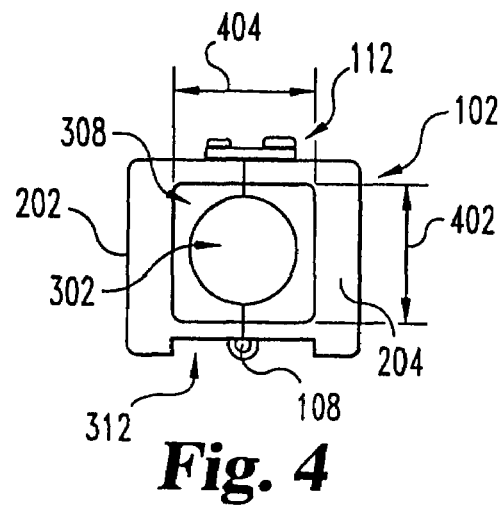
FIG. 4 shows an end view of one end of the packing device of FIG. 1.

A cannula coupling chamber 308 is defined within the cannula coupling portion 102. A coupling portion of a cannula is received within coupling chamber 308 to couple the cannula to the packing device 100. The cannula coupling chamber 308, as shown in FIG. 4, has a height 402 and a width 404 that are sized so as to allow a cannula to couple to the packing device 100. In addition, the rectangular shape of the coupling chamber 308 prevents the separate sections 202, 204 from separating when the packing device 100 is coupled to a cannula. Although a rectangular shaped coupling chamber 308 is shown, it should be appreciated that the coupling chamber 308 can have a different shape in order to accommodate a differently shaped cannula. The coupling portion 102 in another embodiment is shaped such that the coupling portion 102 fits inside the cannula. As should be understood, coupling portion 102 of the packing device 100 can be coupled to other types of devices besides cannula.

Figure 5:
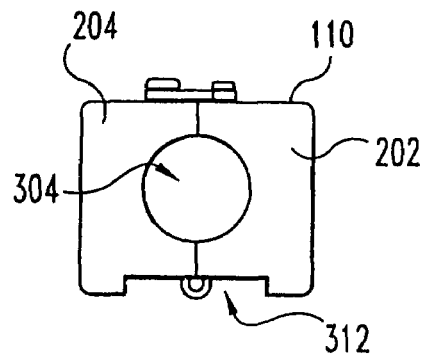
FIG. 5 shows an end view of the other end of the packing device of FIG. 1.

FIG. 5 shows the receiving portion end 110 of the packing device 100. A fusion device is inserted into the packing device 100 through the receiving portion end 110. The packing device 100 further includes a slot 312 defined in both the cannula coupling portion 102 and the insert receiving portion 110. The legs defined by the slot 312 can provide clearance for the packing device 100.

Figure 6:
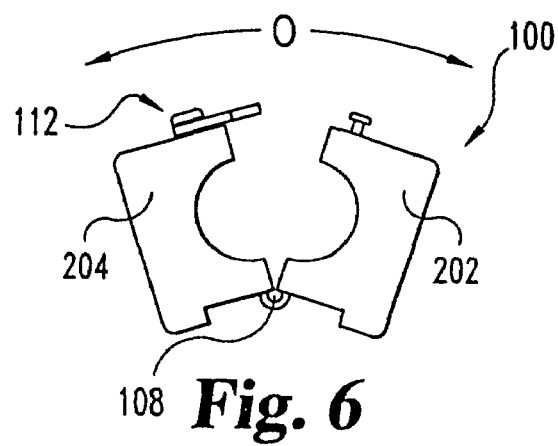
FIG. 6 shows an end view of the packing device of FIG. 1 in an open position.

As shown in FIG. 6, the locking mechanism 112 can be unlocked so that the packing device 100 can be opened. The two separate sections 202, 204 open in an opening direction O by pivoting about the connection member 108. This feature allows the packing device 100 to be easily removed during surgery, and allows for easy cleaning of the cavity 302. It should be understood that the two separate sections 202 and 204 can be coupled together and separated in other manners.

A packing device 700 in accordance with another embodiment of the present invention is shown in FIG. 7. In this embodiment, the access port 106 is defined in only one of two separate sections 702, 704. By having the access port 106 defined in only one of the sections 702, 704, the shape and position of the port 106 can be more accurately defined.

FIG. 8 shows a packing device 800 in accordance with still yet another embodiment. This packing device 800 includes a cannula coupling portion 802, an insert receiving portion 804, access port 106, and cavity 302. The packing device 800 has a uniform maximum outer dimension 806. In addition, the access port 106 has tapered walls 808, which are used to funnel osteogenic material through the port 106. This packing device 800 does not include the cannula coupling chamber 308. Instead, the coupling portion 802 is coupled to a cannula by inserting the coupling portion 802 into a coupling chamber in the cannula (which will be discussed below with reference to FIG. 17).

An end view of a packing device 900 in accordance with another embodiment is shown. The packing device 900 has a circular cavity 902, a circular outer shape 904 at coupling portion 906. The circular cavity 902 coincides with a fusion device that has a circular profile. The circular outer shape 904 at the coupling portion can be coupled to a cannula with a circular coupling member.

A packing device 1000 in accordance with still yet another embodiment is shown in FIG. 10. In this embodiment, the packing device 1000 has a rectangular cavity 1002 to accommodate a fusion device that has a rectangular cross-sectional profile. In particular, the illustrated rectangular cavity 1002 has a square cross-sectional shape. Further, the device 1000 has a rectangular coupling chamber 1006 at coupling portion 1004. The rectangular coupling chamber 1006 accommodates a cannula with rectangular ends. The packing device 1000 further has a rectangular outer shape 1008.

Figure 11:
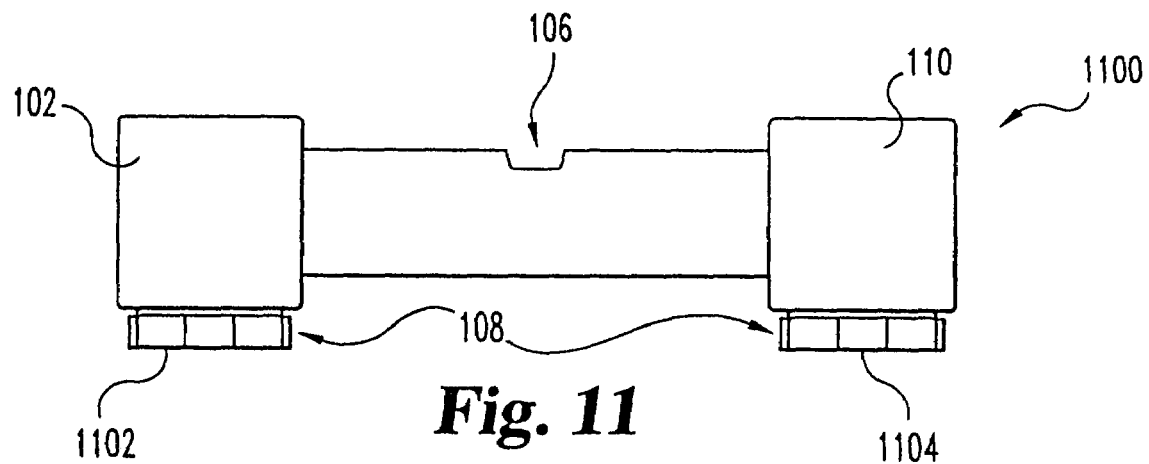
FIG. 11 shows a side view of a packing device with two coupling members.

Still yet another embodiment of a packing device 1100 according to the present invention is shown in FIG. 11. The packing device 1100 has a connection member 108 which includes two hinges 1102 and 1104, respectively provided on the cannula coupling portion 102 and the insert receiving portion 110. By having the hinges 1102, 1104 on separate ends can improve the stability of the packing device 1100.

Figure 12:
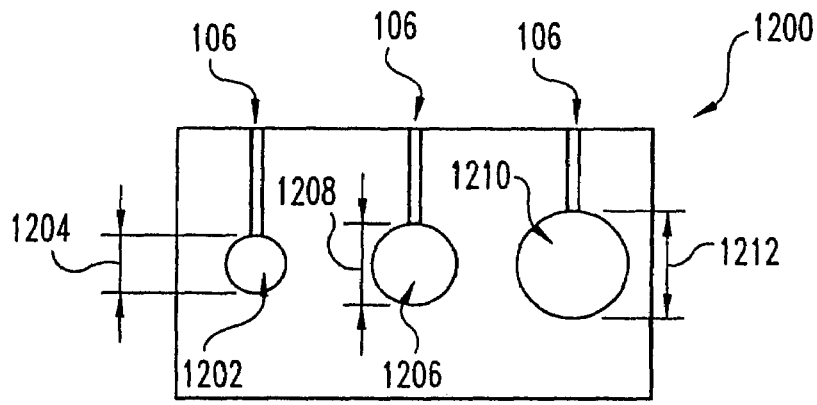
FIG. 12 shows an end view of a packing device with three differently sized cavities.

Depending on the physiology of a patient, fusion devices of different sizes may be required. To solve this problem, a packing device 1200 in accordance with the present invention has multiple cavities. As shown in FIG. 12, the packing device 1200 includes a first cylindrical cavity 1202 with a first diameter 1204, a second cylindrical cavity 1206 with a second diameter 1208, and a third cylindrical cavity 1210 with a third diameter 1212. The diameters 1204, 1208, 1212 of the cavities 1202, 1206, 1210 are different in order to accommodate fusion devices having different outer dimensions. This feature gives a surgeon the flexibility to use differently sized fusion devices depending on the needs of a patient.

Figure 13:
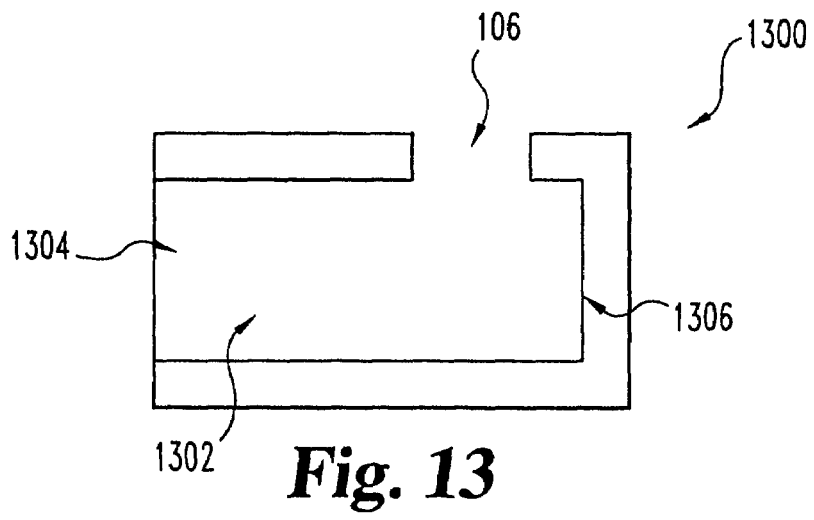
FIG. 13 shows a cross-sectional view of a packing device with one opening.

FIG. 13 shows a packing device 1300 having a cavity 1302 with a single opening 1304 and a closed end 1306. A fusion device is inserted and removed through the single opening 1304. The closed end 1306 acts as a stop for properly positioning the fusion device under access port 106.

A cannula 1400 in accordance with one embodiment of the present invention is shown in FIG. 14. The cannula 1400 at one end has a packing device coupling member 1402. The cannula 1400 at the coupling member 1402 is coupled to the cannula coupling portion 102 of the packing device 100. The cannula 1400 also includes a handle portion 1404, a pair of view ports 1406, and a vertebrae engaging portion 1408. The vertebrae engaging portion 1408 includes a pair of vertebrae engaging members 1410. The vertebrae engaging members 1410 each have serrations 1412, and the serrations 1412 are used to secure the cannula to adjacent vertebrae. The vertebrae engaging members 1410 along with serrations 1412 aid in the attachment of the cannula between adjacent vertebrae. A surgeon can grasp the handle portion 1404 in order to position the cannula 1400. The optional view ports 1406 allow the surgeon to view a fusion device during surgery. It should be appreciated that the cannula 1400 can include a single, multiple, or no view ports 1406. In one embodiment, the cannula 1400 does not include a view port in order to minimize the risk that osteogenic material falling off the fusion device during insertion.

The coupling member 1402 can have different shapes based on the shape of the fusion device. As shown in FIG. 16, the coupling member 1402 in one form of the present invention has a rectangular (square) shape with a height 1606 and a width 1608. The coupling member 1402 is dimensioned such that the coupling member 1402 can fit within the coupling chamber 308 of the packing device 100 and so that the cavity 302 of the packing device 100 aligns with the passage 1602 of the cannula 1400.

The cannula 1400 includes a cylindrical passage 1602 having a diameter 1604. The passage 1602 has a diameter sufficiently large such that the fusion device can pass through. The passage 1602 is aligned with the cavity 302 of the packing device 100 to allow for easy sliding of the fusion device therein. It should be appreciated that the passage 1602 can have various shapes and dimensions so as to match the profile of a fusion device. It should be understood that the cannula 1400 can omit features and/or include additional features.

Figure 17:
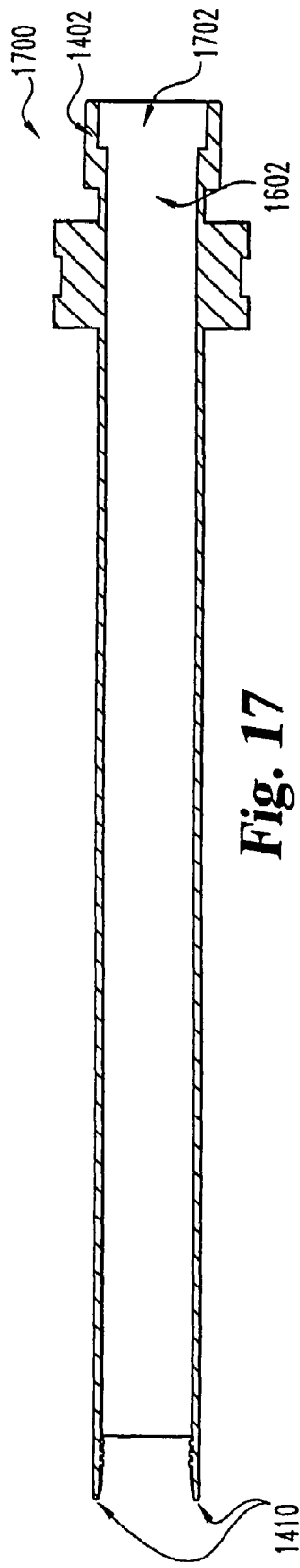
FIG. 17 shows a cross-sectional view of a cannula in accordance with another embodiment.
Figure 18:
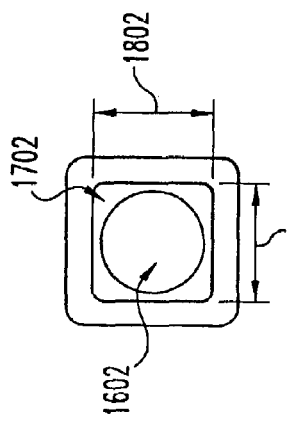
FIG. 18 shows an end view of the cannula of FIG. 17.
Figure 19:
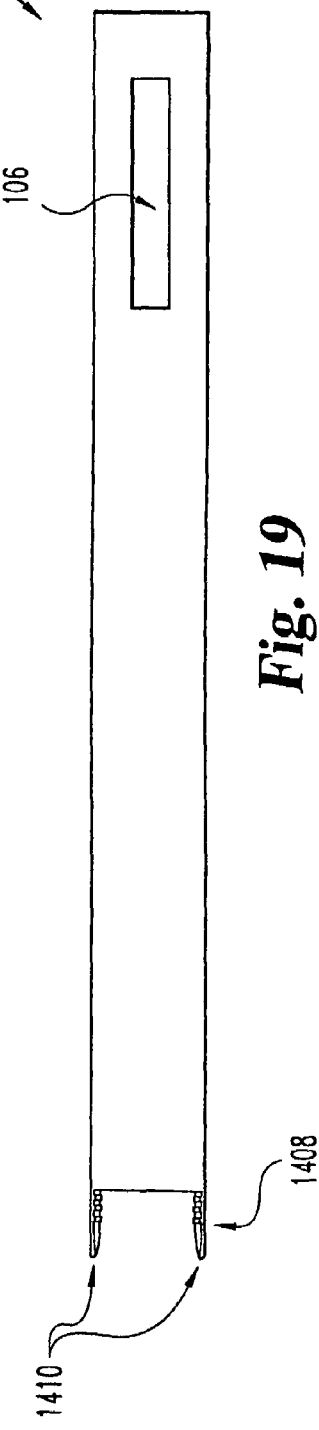
FIG. 19 shows a top view of a packing device integrated into a cannula.

A cannula 1700 in accordance with another embodiment is shown in FIG. 17. The coupling member 1402 includes a coupling chamber 1702 in which the coupling portion 802 of packing device 800 (FIG. 8) is inserted and coupled to the cannula 1700. Further, the cannula 1700 does not include a view port 1406. An end view of the coupling portion 1402 is shown in FIG. 18. The coupling chamber 1702 has a square shape with a width 1802 and a length 1804 which can accommodate the outer dimensions of the coupling portion 802 of the packing device 800. In still yet another embodiment, the packing device 100 and the cannula 1400 are combined into a single simplified device 1900 as shown in FIG. 19. The access port 106 is defined in the cannula 1900. A fusion device is inserted into device 1900, and osteogenic material is packed through port 106 onto the fusion device.

An inserter 2000 according to one embodiment of the present invention is shown in FIG. 20. The inserter 2000 includes a shaft 2002, a coupling end 2004 at one end of the shaft 2002, and a handle portion 2006 provided at the other end of the shaft 2002. A coupling mechanism 2008 is provided within the shaft 2002 for coupling fusion a device to the inserter 2000. The shaft 2002 includes a tapered portion 2010 and depth markings 2012. The coupling end 2004 has a ridge 2014, and the handle portion 2006 has an opening 2016 in which a portion of the coupling mechanism 2008 is provided. Further, the handle portion 2006 includes a roughened surface 2018 and a connector 2020. The depth indicators 2012 are used to indicate the depth of the inserter 2000 during surgery. The roughened surface 2018 on the handle portion 2006 helps to improve grip during surgery.

As shown in FIGS. 21-22, the inserter 2000 includes a passageway 2102 in which the coupling mechanism 2008 passes through. The coupling mechanism 2008 includes a shaft 2104 with a threaded portion 2106 at the coupling end 2004 and a knob 2108. It should be appreciated that the shaft 2104 can have the threaded portion 2106 extend only over a portion of the shaft 2104 or extend over the entire length of the shaft 2104. It should be understood that other types of coupling members can be incorporated into the inserter 2000 depending on the type of fusion device used.

Numerous types of fusion devices can be used in accordance with the present invention, including for example those disclosed in WO99/29271 published Jun. 17, 1999, which is hereby incorporated herein by reference in its entirety. FIG. 23 shows one such type of fusion device 2300. The fusion device 2300 includes a first end piece 2302, a second end piece 2304, and a central element 2306 coupling the two end pieces 2302, 2304 together. A cavity 2308 is formed between the two end pieces 2302, 2304 in which osteogenic material is packed. The first end piece 2302 has a width 2312, and the second end piece 2304 has a width 2314. The cavity 2308 between the end pieces 2302, 2304 has a width 2316, which approximately corresponds to the length 210 of the opening 106 in the packing device, and the fusion device 2300 has an overall length 2318. This arrangement allows a surgeon to have complete access to fill the cavity 2308 of the fusion device 2300. It should be understood that fusion devices with configurations different than the one shown can also be used.

As shown in FIG. 24, one of the end pieces 2302 includes apertures 2402 through which osteogenic material can pass through. The second end 2304 includes a notch 2502 in which the ridges 2014 of the inserter 2000 are coupled. In addition, the fusion device 2300 includes a threaded hole 2504, which engages the threaded portion 2106 of the coupling mechanism 2008. It should be understood that the fusion device 2300 can be coupled to the inserter 200 in other generally known manners.

FIG. 26 shows the inserter 2000 coupled to the fusion device 2300 to form an inserter-fusion device assembly 2600. The ridge 2014 of the inserter 2000 engages the groove 2502 in the fusion device 2300. This engagement allows the fusion device 2300 to be screwed between adjacent vertebrae.

Figure 27:
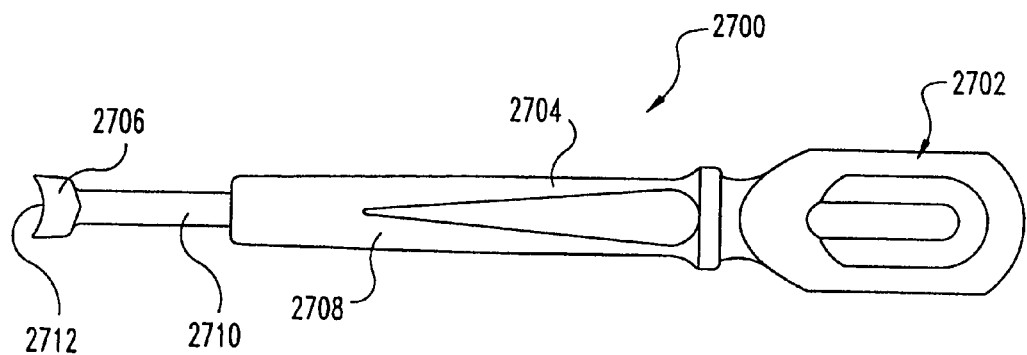
FIG. 27 shows a top view of a compactor in accordance with one embodiment of the present invention.
Figure 28:
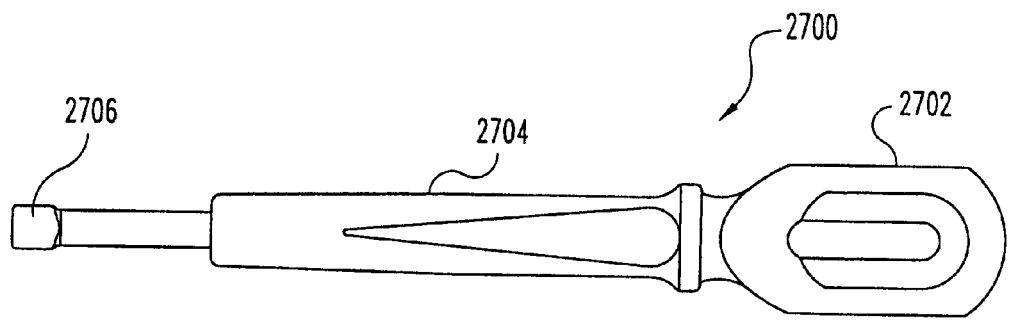
FIG. 28 shows a side view of the compactor of FIG. 27.
Figure 29:
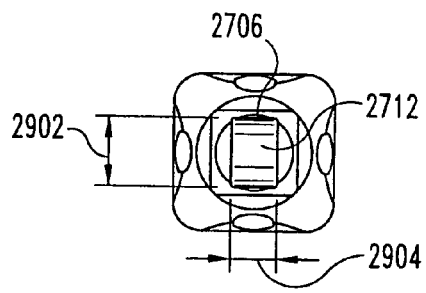
FIG. 29 shows an end view of the compactor of FIG. 27.

A compactor 2700 in accordance with one embodiment of the present invention is shown in FIGS. 27-29. The compactor 2700 includes a handle portion 2702, a shaft 2704 coupled to the handle portion 2702, and a plunger 2706 coupled to the shaft 2704. The shaft 2704 includes a tapered portion 2708 coupled to the handle portion 2702 and a non-tapered portion 2710 coupled to the plunger 2706. The plunger 2706 includes a contacting surface 2712. In one embodiment, the contacting surface is curved in order to improve packing of material around the fusion device 2300. The curvature of the contacting surface 2712 matches the curvature of the cavity 302 of the packing device 100 so that the osteogenic material can be uniformly provided around the fusion device 2300. As shown in FIG. 29, the contacting surface 2712 of the plunger 2706 has a length 2902 and a width 2904. In one form, this length 2902 is slightly smaller than the width 212 of the port 106 so that the plunger 2706 can fit through the port 106. This profile of the plunger 2706 roughly corresponds to the size of the port 106 in the packing device 100. This profile ensures that the fusion device 2300 is adequately packed with osteogenic material.

Figure 30:
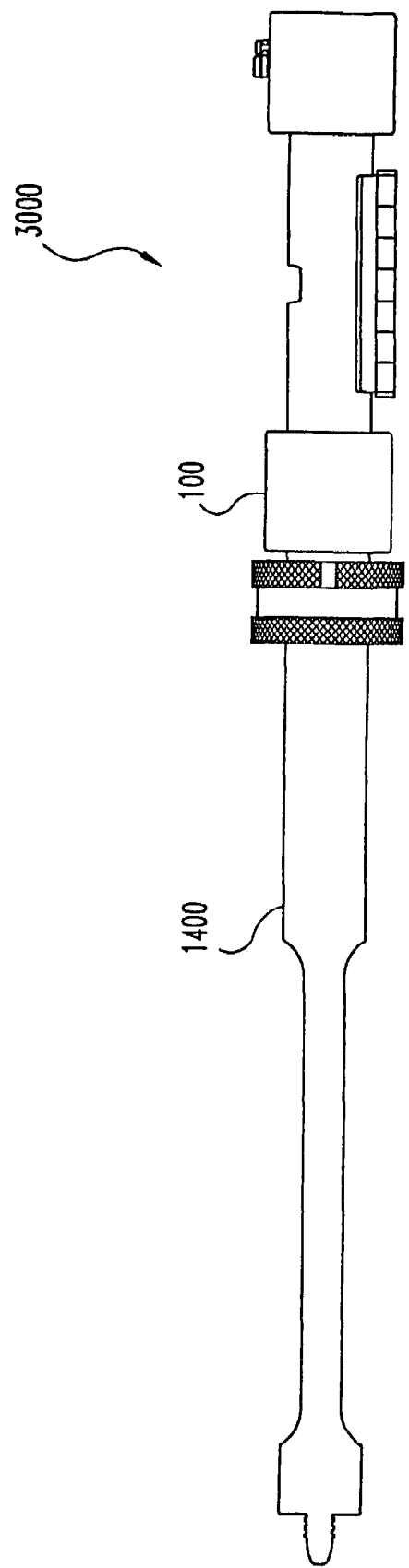
FIG. 30 shows a side view of an assembly with the cannula of FIG. 14 coupled to the packing device of FIG. 1.
Figure 31:
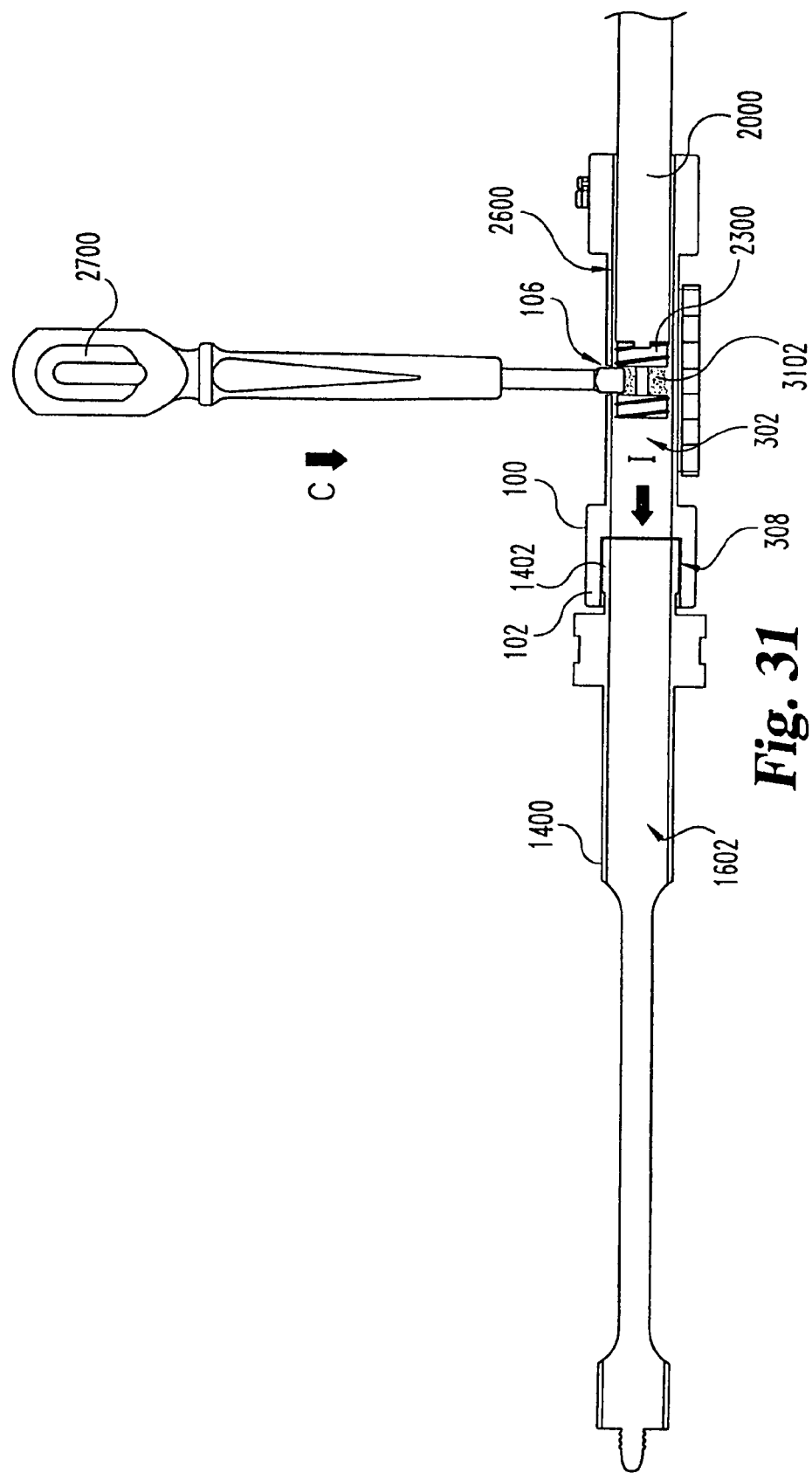
FIG. 31 shows a cross-sectional view of the assembly of FIG. 30.

A cannula-packing device assembly 3000 is shown in FIG. 30. The assembly 3000 includes the packing device 100 and the cannula 1400 coupled to the packing device 100. A cross-sectional view of the coupled packing device 100 and cannula 1400 is shown in FIG. 31. The cannula coupling portion 102 with coupling chamber 308 is coupled to packing device coupling member 1402. The inserter 2000 is coupled to the fusion device 2300, and the fusion device 2300 along with the inserter 2000 are inserted into the packing device in direction I. The compactor 2700 is moved in direction C through port 106 in order to compact osteogenic material 3102 around the fusion device 2300. As shown, the cavity 302 of the packing device 100 is aligned with the passage 1602 of the cannula 1400 so that the fusion device 2300 can be easily slid from the packing device 100 into the cannula 1400.

A method for packing osteogenic material in accordance with one embodiment of the present invention will now be described in reference to FIGS. 32-39. In stage 3200, as shown in FIG. 32, the cannula 1400 is inserted in direction I into an intervertebral space 3206 between adjacent vertebrae 3202, 3204. The vertebrae engaging members 1410 engage the adjacent vertebrae 3202, 3204. The serrations 1412 reduce slippage of the cannula 1400 from the vertebrae 3202, 3204. In stage 3300, the packing device 100 is moved in direction I and coupled to the cannula 1400. The inserter-fusion device assembly 2600 is inserted in direction I into the insert receiving portion 100 of the fusion device 100 in stage 3400. The cavity 2308 of the fusion device 2300 is aligned with the access port 106 of the packing device 100 as shown in FIG. 35. In stage 3500, osteogenic material 3102 is packed into the cavity 2308 of the fusion device 2300. The compactor 2700 is moved in direction C to press the osteogenic material 3102 into the cavity 2308. The osteogenic material may be selected from among many known to those skilled in the art. For example, the osteogenic material may comprise minerals such as calcium phosphate or calcium sulfate minerals, bone, including xenograft, allograft or autograft bone, or the like. The osteogenic material may also comprise demineralized bone matrix (DBM), osteoinductive factors such as bone morphogenetic proteins (e.g. human BMP-2 or human BMP-7 or heterodimers thereof) whether recombinantly produced or purified from tissues, LIM mineralization proteins (LMPs), or the like. The osteogenic material may also comprise a binder material such as blood, clottable blood fractions, platelet gel, collagen, gelatin, carboxymethyl cellulose, or other similar materials that will serve to bind together harder particles or materials such as mineral particles (e.g. bone or synthetic mineral particles) so as to create a three-dimensionally stable mass when compacted on the spinal fusion implant. Such binder can be admixed with other materials in the osteogenic composition prior to or after loading the other materials into the cavity 2308. As will be appreciated, the binder may be a hardenable material such as a gel-forming, clottable, or cross-linkable material, or can be a material which is not hardenable but nonetheless serves to bind particles together to provide integrity to the compacted osteogenic mass.

Figure 38:
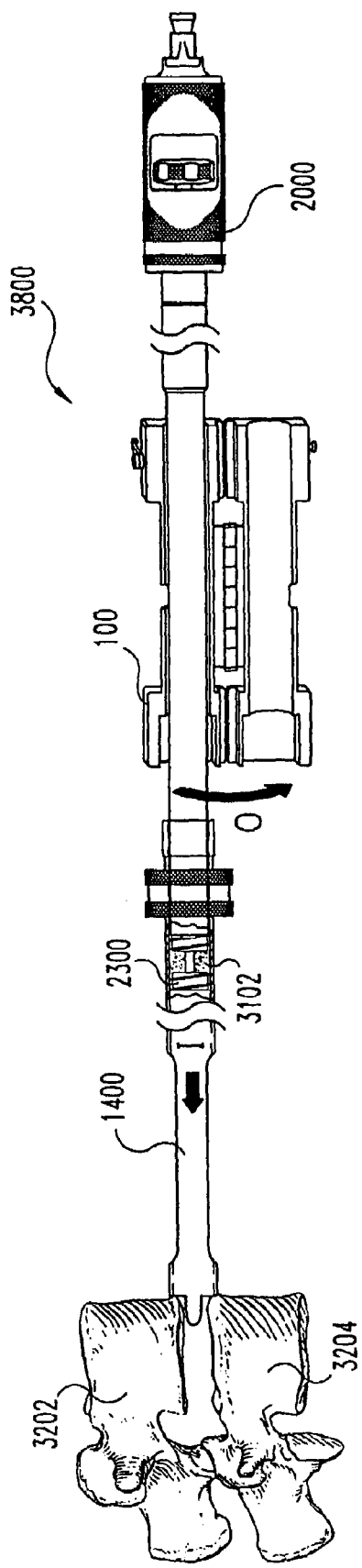
FIG. 38 shows a partial cross-sectional view of the packing device removed from the inserter.
Figure 39:
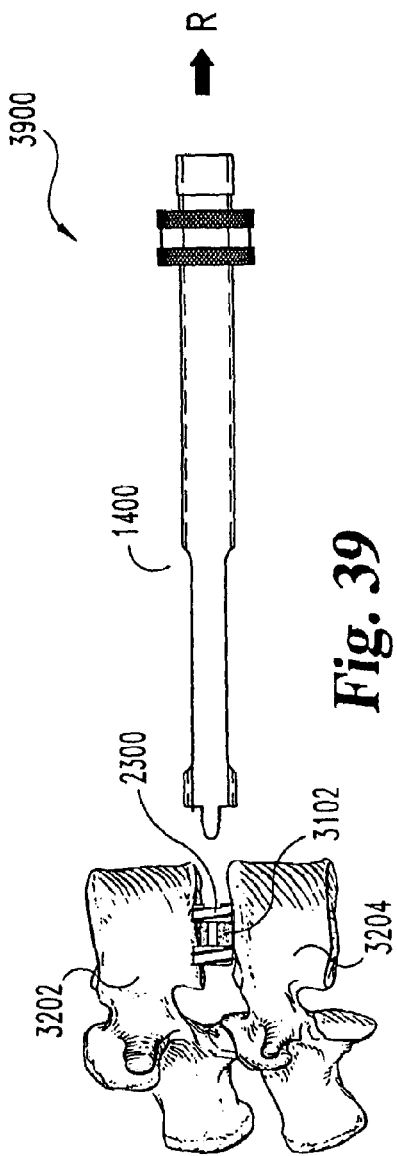
FIG. 39 shows a side view of the cannula removed from the vertebrae.

After the osteogenic material 3102 is compacted around the fusion device 2300, the inserter 2000 is moved in direction I in stage 3600 so that the fusion device 2300 is moved into the cannula 1400 (FIG. 36). After the fusion device 2300 is within the cannula 1400, the packing device 100 is moved in direction R, as shown in FIG. 37, along the inserter 2000 to decouple the packing device 100 from the cannula 1400 in stage 3700. The locking mechanism 112 is unlocked. Then, the packing device 100 is opened in direction O and removed from the inserter 2000 in stage 3800. As shown in FIG. 38, the inserter 2000 then moves the fusion device 2300 in direction I so that the fusion device 2300 along with the osteogenic material 3102 can be inserted into the intervertebral space 3206. As shown in FIG. 39, after the fusion device 2300 is inserted between the vertebrae 3202, 3204, the cannula 1400 is removed by moving the cannula 1400 in direction R in stage 3900.

Figure 40:
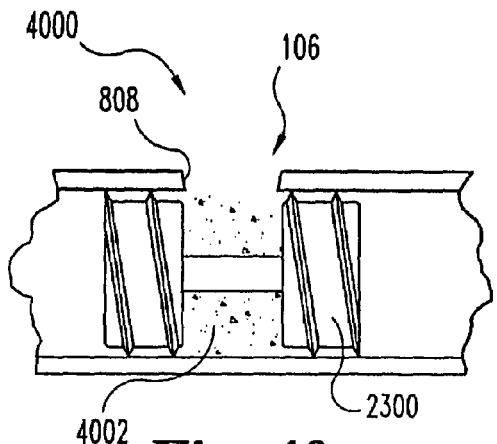
FIG. 40 shows a partial cross-sectional view of a fusion device with bone chips provided therein.
Figure 41:
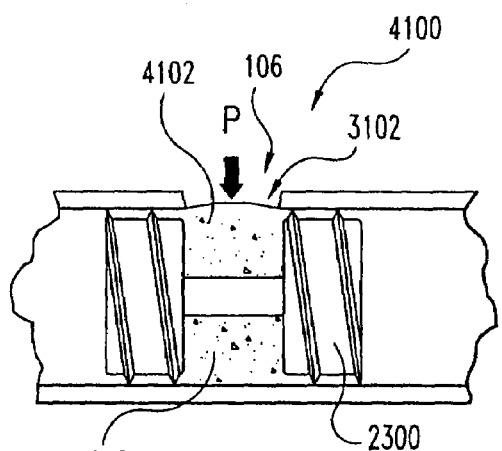
FIG. 41 shows a partial cross-sectional view of the fusion device of FIG. 40 with a binder provided therein.

One method for providing osteogenic material 3102 around the fusion device 2300 in accordance with another embodiment of the present invention is shown in FIGS. 40-41. In stage 4000, osteogenic material chips 4002 such as bone chips or mineral particles are packed through port 106 around the fusion device 2300. In stage 4100, a binder 4102 is poured in direction P through port 106 to form osteogenic material 3102. The access portion 106 has tapered walls 808, which funnels the binder 4102 through the port 106. The binder and chips or particles are then admixed and compacted together around the fusion device 2300.

In another specific form of the invention, autograft chips are loaded through port 106. Blood residual on the bone chips and/or blood from the patient or a donor may serve as a binder in this method. After a short time, the blood clots and the fusion device 2300 with the osteogenic material 3102 is removed. The clotted blood acts as a binder and retains the bone chips during implantation. As will be understood, clotting of the blood may be facilitated by the addition of appropriate factors such as thrombin, etc. In another form, platelet gel is used as a binder to provide an even stronger cohesiveness. Calcium phosphate cements with or without osteogenic growth factors such as BMP are used in still yet another form.

As noted above, the osteogenic material 3102 can include autograft bone, allograft bone and/or demineralized bone. Likewise, the chips 4002 can include allograft, autograft, and/or demineralized bone chips. The osteogenic material 3102 such as bone chips, once inserted can optionally be of sufficient strength provide some additional compressive properties to maintain the intervertebral disc space 3206 after distraction. In another embodiment, a self setting cement is used alone or in combination with bone chips. The self setting cement offers superior compressive properties.

Figure 42:
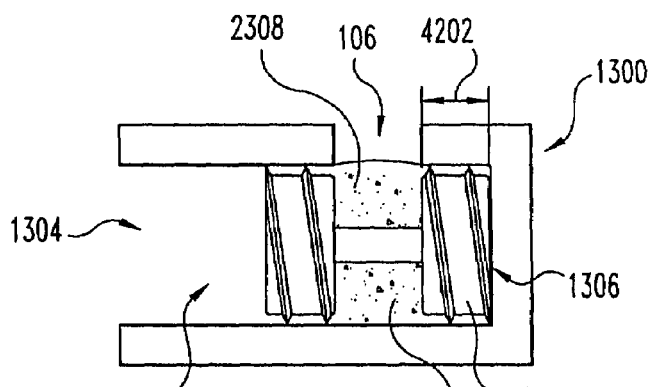
FIG. 42 shows a partial cross-sectional view of a fusion device provided in the packing device of FIG. 13.

Another embodiment for a method of providing osteogenic material around a fusion device will now be described with reference to FIG. 42. The packing device 1300 (FIG. 13) is shown in FIG. 42. The fusion device 2300 is inserted into the cavity 1302 of the packing device 1300. The depth 4202 of the cavity 1302 between the closed end 1306 and the access port 106 is substantially equal to the width 2312, 2314 of one of the end pieces 2302, 2304 of the fusion device 2300. This distance 4202 allows the cavity 2308 of the fusion device 2300 to be properly aligned under the access port 106. Once inserted, osteogenic material 3102 is poured and/or packed into the cavity 2308 of the fusion device 2300. After the osteogenic material 3102 is provided around the fusion device 2300, the fusion device 2300 is then removed out of the opening 1304. The fusion device 2300 in one form is inserted and removed using the inserter 2000. It should be understood that the fusion device 2300 can be inserted and removed from the packing device 1300 in other manners such as by hand. Once removed, the fusion device 2300 can then be directly inserted into the intervertebral space 3206 or can be indirectly inserted by using the cannula 1400.

Figure 43:
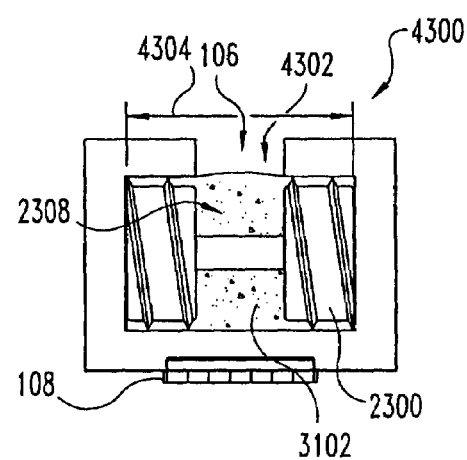
FIG. 43 shows a partial cross-sectional view of a packing device with closed ends.

A method according to still yet another embodiment of the present invention will now be described with reference to FIG. 43. A packing device having a closed cavity 4302 is used. The packing device 4300 is opened along coupling mechanism 108 in a manner similar to the one shown in FIG. 6. The fusion device 2300 is then inserted into the cavity 4302, and the fusion device 4300 is then closed. As shown in FIG. 43, the length 4304 of the cavity 4302 is slightly larger than the length of the fusion device 2300 such that the cavity 2308 of the fusion device 2300 is aligned with the access port 106 of the packing device 4300. Osteogenic material 3102 is then packed and/or poured around the fusion device 2300. Then, the packing device 4300 is opened to remove the fusion device 2300.

While specific embodiments of the present invention have now been shown and described in detail, the breadth and scope of the present invention should not be limited by the above described exemplary embodiments, but should be defined only in accordance with the following claims and their equivalents. All changes and modifications that come within the spirit of the invention are desired to be protected.

What is claimed is:

1. A method of loading osteogenic material onto a fusion device, comprising:
    providing a fusion device having a predetermined size and shape including a length and a width, the fusion device having a central portion extending between opposite end portions, the central portion extending along the length of the fusion device and defining a cavity;
    inserting the fusion device having the predetermined size and shape into a cavity of a packing device that includes an access port, in which the fusion device has an outside;
    providing the osteogenic material through the access port and onto the fusion device, said providing including packing the osteogenic material around the outside of the fusion device and into the cavity defined by the central portion of the fusion device;
    coupling the packing device to a cannula in which a passage of the cannula is aligned with the cavity of the packing device;
    sliding the fusion device into the passage of the cannula after said providing; and
    removing the packing device from the cannula after said sliding.

2. The method of claim 1, wherein said providing includes packing the osteogenic material onto the fusion device with a compactor.

3. The method of claim 1, wherein said providing includes pouring the osteogenic material through the access port.

4. The method of claim 1, wherein said providing includes packing osteogenic material chips through the access port and pouring a binder through the access port.

5. The method of claim 4, wherein the chips include autograft bone.

6. The method of claim 4, wherein the chips include allograft bone.

7. The method of claim 4, wherein the chips include demineralized bone.

8. The method of claim 4, wherein the binder includes blood.

9. The method of claim 4, wherein the binder is selected from a group consisting of platelet gel, collagen, gelatin, hyaluronic acid, calcium sulfate, carboxymethyl cellulose, calcium phosphate, peptides, and polymers.

10. The method of claim 1, wherein said providing includes pouring a self-setting cement through the access port.

11. The method of claim 1, further comprising coupling the fusion device to an inserter.

12. The method of claim 1, further comprising inserting the fusion device between adjacent vertebrae after said providing the osteogenic material through the access port and onto the fusion device.

13. The method of claim 1, further comprising inserting the cannula at an intervertebral space between adjacent vertebrae.

14. The method of claim 13, wherein said inserting the cannula precedes said providing the osteogenic material.

15. The method of claim 1, wherein the packing device is integrated in the cannula.

16. The method of claim 1, further comprising:
    the packing device including at least two sections locked together with a locking mechanism; and
    opening the packing device after said providing by unlocking the locking mechanism to separate apart the at least two sections of the packing device.

17. The method of claim 1, further comprising:
    inserting the fusion device between the adjacent vertebrae by sliding the fusion device from the cannula.

18. A method of loading osteogenic material onto a fusion device, comprising:
    inserting the fusion device into a cavity of a packing device that includes an access port, in which the fusion device has an outside;

providing the osteogenic material through the access port and onto the fusion device, said providing including packing the osteogenic material around the outside of the fusion device;
closing the packing device around the fusion device before said providing;
coupling the packing device to a cannula in which a passage of the cannula is aligned with the cavity of the packing device;
sliding the fusion device into the passage of the cannula after said providing; and
removing the packing device from the cannula after said sliding.

19. A method of loading osteogenic material onto a fusion device, comprising:
inserting the fusion device into a cavity of a packing device that includes an access port;
coupling the fusion device to an inserter before said inserting, and wherein said inserting includes sliding the fusion device into the packing device with the inserter;
providing the osteogenic material through the access port and onto the fusion device;
coupling the packing device to a cannula in which a passage of the cannula is aligned with the cavity of the packing device;
sliding the fusion device into the passage of the cannula after said providing; and
removing the packing device from the cannula after said sliding.

20. The method of claim 19, wherein said removing includes sliding the fusion device along the inserter and opening the packing device by hingedly separating two portions of the packing device.

21. A method of loading osteogenic material onto a fusion device, comprising:
inserting the fusion device into a cavity of a packing device that includes an access port, in which the fusion device has an outside;
providing the osteogenic material through the access port and onto the fusion device, said providing including packing the osteogenic material around the outside of the fusion device;
coupling the packing device to a cannula in which a passage of the cannula is aligned with the cavity of the packing device;
sliding the fusion device into the passage of the cannula after said providing; and
removing the packing device from the cannula after said sliding; and
the fusion device including two end pieces, a central element joining the two end pieces together, and a cavity defined between the two end pieces along the central element; and
said providing the osteogenic material includes packing the osteogenic material in the cavity around the central element with a compactor.

22. A method of loading osteogenic material onto a fusion device, comprising:
providing a fusion device having a predetermined size and shape including a length and a width, and wherein the fusion device has a central portion extending between opposite end portions, the central portion extending along the length of the fusion device and defining a cavity;
inserting the fusion device having the predetermined size and shape into a cavity of a packing device that includes an access port;
providing the osteogenic material through the access port and onto the fusion device, and wherein the providing the osteogenic material through the access port and onto the fusion device comprises packing the osteogenic material into the cavity defined by the central portion of the fusion device;
coupling the packing device to a cannula in which a passage of the cannula is aligned with the cavity of the packing device;
sliding the fusion device into the passage of the cannula after said providing; and
removing the packing device from the cannula after said sliding.

23. A method of loading osteogenic material onto a fusion device, comprising:
providing a fusion device having a predetermined size and shape including a length and a width;
inserting the fusion device having the predetermined size and shape into a cavity of a packing device that includes an access port;
providing the osteogenic material through the access port and onto the fusion device;
coupling the packing device to a cannula in which a passage of the cannula is aligned with the cavity of the packing device;
sliding the fusion device into the passage of the cannula after said providing; and
removing the packing device from the cannula after said sliding; and
coupling the fusion device to an inserter instrument before the inserting, and wherein the inserting includes positioning the fusion device in the packing device using the inserter instrument.

24. A method, comprising:
providing a fusion device having a predetermined size and shape including a length and a width, and wherein the fusion device has a central portion extending between opposite end portions, the central portion extending along the length of the fusion device and defining a cavity;
inserting the fusion device having the predetermined size and shape inside of a packing device;
packing osteogenic material onto the fusion device located inside of the packing device, and wherein the packing comprises loading the osteogenic material into the cavity defined by the central portion of the fusion device;
sliding the fusion device into the passage of a cannula after said packing;
coupling the packing device to the cannula in which the passage of the cannula is aligned with the packing device before said sliding; and
decoupling the packing device from the cannula after said sliding.

* * * * *